(12) United States Patent
Kerr

(10) Patent No.: US 12,167,886 B2
(45) Date of Patent: *Dec. 17, 2024

(54) ACCURATE JAW CLOSURE FORCE IN A CATHETER BASED INSTRUMENT

(71) Applicant: Covidien LP, Mansfield, MA (US)

(72) Inventor: Duane E. Kerr, Loveland, CO (US)

(73) Assignee: Covidien LP, Mansfield, MA (US)

( * ) Notice: Subject to any disclaimer, the term of this patent is extended or adjusted under 35 U.S.C. 154(b) by 150 days.

This patent is subject to a terminal disclaimer.

(21) Appl. No.: 17/672,812

(22) Filed: Feb. 16, 2022

(65) Prior Publication Data

US 2022/0226038 A1    Jul. 21, 2022

Related U.S. Application Data

(63) Continuation of application No. 12/786,589, filed on May 25, 2010, now Pat. No. 11,278,345.

(51) Int. Cl.
*A61B 18/14* (2006.01)
*A61B 34/00* (2016.01)
(Continued)

(52) U.S. Cl.
CPC .......... *A61B 18/1445* (2013.01); *A61B 34/71* (2016.02); *A61B 2017/00314* (2013.01);
(Continued)

(58) Field of Classification Search
CPC ..... A61B 18/14; A61B 18/1445; A61B 18/28; A61B 17/28; A61B 17/29; A61B 17/2804; A61B 17/2812; A61B 17/2816; A61B 17/2841; A61B 2017/00314; A61B 2017/2845; A61B 2017/2901; A61B 17/282; A61B 2017/00327; A61B 2017/2905

See application file for complete search history.

(56) References Cited

U.S. PATENT DOCUMENTS

D263,020 S   2/1982  Rau, III
D295,893 S   5/1988  Sharkany et al.
(Continued)

FOREIGN PATENT DOCUMENTS

DE    2415263 A1   10/1975
DE    2514501 A1   10/1976
(Continued)

OTHER PUBLICATIONS

Int'l Search Report EP 07 021647.8 dated May 2, 2008.
(Continued)

*Primary Examiner* — Vi X Nguyen

(57) ABSTRACT

A surgical instrument includes a housing, an end effector and an elongated shaft extending therebetween. The end effector is movable between open and closed configurations. The elongated shaft includes a distal portion that is movable between aligned and articulated configurations. The surgical instrument further includes a driving assembly that induces motion in the end effector between open and closed configuration and maintains a closure pressure in the range of about 3 kg/cm$^2$ to about 16 kg/cm$^2$ between aligned and articulated configurations of the elongated shaft.

9 Claims, 11 Drawing Sheets

(51) Int. Cl.
*A61B 17/00* (2006.01)
*A61B 17/29* (2006.01)

(52) U.S. Cl.
CPC ............... *A61B 2017/00323* (2013.01); *A61B 2017/2925* (2013.01)

(56) References Cited

U.S. PATENT DOCUMENTS

| | | |
|---|---|---|
| D295,894 S | 5/1988 | Sharkany et al. |
| 5,179,934 A | 1/1993 | Nagayoshi et al. |
| 5,250,056 A | 10/1993 | Hasson |
| D348,930 S | 7/1994 | Olson |
| 5,403,342 A | 4/1995 | Tovey et al. |
| 5,452,836 A | 9/1995 | Huitema et al. |
| 5,456,684 A | 10/1995 | Schmidt et al. |
| 5,549,637 A | 8/1996 | Crainich |
| 5,562,701 A | 10/1996 | Huitema et al. |
| 5,620,415 A | 4/1997 | Lucey et al. |
| 5,620,459 A | 4/1997 | Lichtman |
| 5,626,609 A | 5/1997 | Zvenyatsky et al. |
| D384,413 S | 9/1997 | Zlock et al. |
| 5,673,840 A | 10/1997 | Schulze et al. |
| 5,673,841 A | 10/1997 | Schulze et al. |
| 5,752,973 A | 5/1998 | Kieturakis |
| 5,797,537 A | 8/1998 | Oberlin et al. |
| 5,817,119 A | 10/1998 | Klieman et al. |
| D424,694 S | 5/2000 | Tetzlaff et al. |
| D425,201 S | 5/2000 | Tetzlaff et al. |
| 6,126,665 A | 10/2000 | Yoon |
| 6,139,563 A | 10/2000 | Cosgrove, III et al. |
| D449,886 S | 10/2001 | Tetzlaff et al. |
| D457,958 S | 5/2002 | Dycus et al. |
| D457,959 S | 5/2002 | Tetzlaff et al. |
| 6,663,641 B1 | 12/2003 | Kovac et al. |
| D493,888 S | 8/2004 | Reschke |
| D496,997 S | 10/2004 | Dycus et al. |
| D499,181 S | 11/2004 | Dycus et al. |
| 6,821,285 B2 | 11/2004 | Laufer et al. |
| D509,297 S | 9/2005 | Wells |
| D525,361 S | 7/2006 | Hushka |
| 7,083,618 B2 | 8/2006 | Couture et al. |
| 7,101,372 B2 | 9/2006 | Dycus et al. |
| D531,311 S | 10/2006 | Guerra et al. |
| D533,942 S | 12/2006 | Kerr et al. |
| D535,027 S | 1/2007 | James et al. |
| 7,156,846 B2 | 1/2007 | Dycus et al. |
| 7,195,631 B2 | 3/2007 | Dumbauld |
| D541,418 S | 4/2007 | Schechter et al. |
| D541,938 S | 5/2007 | Kerr et al. |
| 7,320,700 B2 | 1/2008 | Cooper et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,487,780 B2 | 2/2009 | Hooven |
| 7,540,872 B2 | 6/2009 | Schechter et al. |
| 7,575,144 B2 | 8/2009 | Ortiz et al. |
| 7,588,176 B2 | 9/2009 | Timm et al. |
| 7,615,067 B2 | 11/2009 | Lee et al. |
| 7,628,791 B2 | 12/2009 | Garrison et al. |
| 7,670,334 B2 | 3/2010 | Hueil et al. |
| 7,703,653 B2 | 4/2010 | Shah et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,799,028 B2 | 9/2010 | Schechter et al. |
| 8,092,451 B2 | 1/2012 | Schechter et al. |
| 8,112,871 B2 | 2/2012 | Brandt et al. |
| 8,133,254 B2 | 3/2012 | Dumbauld et al. |
| 8,162,965 B2 | 4/2012 | Reschke et al. |
| 8,187,273 B2 | 5/2012 | Kerr et al. |
| 8,226,650 B2 | 7/2012 | Kerr |
| 8,251,994 B2 | 8/2012 | McKenna et al. |
| 8,252,626 B2 | 8/2012 | Cho et al. |
| 8,266,783 B2 | 9/2012 | Brandt et al. |
| 8,277,446 B2 | 10/2012 | Heard |
| 8,287,536 B2 | 10/2012 | Mueller et al. |
| 8,292,067 B2 | 10/2012 | Chowaniec et al. |
| 8,292,886 B2 | 10/2012 | Kerr et al. |
| 8,323,310 B2 | 12/2012 | Kingsley |
| 8,343,150 B2 | 1/2013 | Artale |
| 8,343,151 B2 | 1/2013 | Siebrecht et al. |
| 8,357,159 B2 | 1/2013 | Romero |
| 8,388,647 B2 | 3/2013 | Nau, Jr. et al. |
| 8,409,246 B2 | 4/2013 | Kerr et al. |
| 8,409,247 B2 | 4/2013 | Garrison et al. |
| 8,425,511 B2 | 4/2013 | Olson |
| 8,430,876 B2 | 4/2013 | Kappus et al. |
| 8,430,877 B2 | 4/2013 | Kerr et al. |
| 8,439,911 B2 | 5/2013 | Mueller |
| 8,439,913 B2 | 5/2013 | Horner et al. |
| 8,469,991 B2 | 6/2013 | Kerr |
| 8,469,992 B2 | 6/2013 | Roy et al. |
| 8,480,671 B2 | 7/2013 | Mueller |
| 8,491,624 B2 | 7/2013 | Kerr et al. |
| 8,491,625 B2 | 7/2013 | Horner |
| 8,491,626 B2 | 7/2013 | Roy et al. |
| 8,512,336 B2 | 8/2013 | Couture |
| 8,512,371 B2 | 8/2013 | Kerr et al. |
| 8,540,749 B2 | 9/2013 | Garrison et al. |
| 8,556,929 B2 | 10/2013 | Harper et al. |
| 8,568,397 B2 | 10/2013 | Horner et al. |
| 8,568,412 B2 | 10/2013 | Brandt et al. |
| 8,585,736 B2 | 11/2013 | Horner et al. |
| 8,597,295 B2 | 12/2013 | Kerr |
| 8,623,018 B2 | 1/2014 | Horner et al. |
| 8,647,343 B2 | 2/2014 | Chojin et al. |
| 8,668,689 B2 | 3/2014 | Dumbauld et al. |
| 8,672,939 B2 | 3/2014 | Garrison |
| 8,679,114 B2 | 3/2014 | Chapman et al. |
| 8,679,115 B2 | 3/2014 | Reschke |
| 8,740,898 B2 | 6/2014 | Chojin et al. |
| 8,777,945 B2 | 7/2014 | Floume et al. |
| 8,808,288 B2 | 8/2014 | Reschke |
| 8,858,553 B2 | 10/2014 | Chojin |
| 8,961,504 B2 | 2/2015 | Hoarau et al. |
| 8,968,358 B2 | 3/2015 | Reschke |
| 8,968,359 B2 | 3/2015 | Kerr et al. |
| 9,024,237 B2 | 5/2015 | Bonn |
| 9,060,798 B2 | 6/2015 | Harper et al. |
| 9,192,430 B2 | 11/2015 | Rachlin et al. |
| 9,585,709 B2 | 3/2017 | Krapohl |
| 9,820,806 B2 | 11/2017 | Lee et al. |
| 10,265,118 B2 | 4/2019 | Gerhardt |
| 11,278,345 B2* | 3/2022 | Kerr ............... A61B 18/1445 |
| 2002/0188294 A1 | 12/2002 | Couture et al. |
| 2003/0018332 A1 | 1/2003 | Schmaltz et al. |
| 2003/0229344 A1 | 12/2003 | Dycus et al. |
| 2004/0068274 A1 | 4/2004 | Hooven |
| 2004/0194790 A1 | 10/2004 | Laufer |
| 2004/0254573 A1 | 12/2004 | Dycus et al. |
| 2005/0107785 A1 | 5/2005 | Dycus et al. |
| 2005/0165415 A1 | 7/2005 | Wales |
| 2006/0064085 A1 | 3/2006 | Schechter et al. |
| 2006/0129146 A1 | 6/2006 | Dycus et al. |
| 2007/0062017 A1 | 3/2007 | Dycus et al. |
| 2007/0142833 A1 | 6/2007 | Dycus et al. |
| 2007/0142969 A1 | 6/2007 | Devengenzo et al. |
| 2007/0158385 A1 | 7/2007 | Hueil et al. |
| 2008/0308602 A1 | 12/2008 | Timm et al. |
| 2008/0308603 A1 | 12/2008 | Shelton et al. |
| 2008/0308606 A1 | 12/2008 | Timm et al. |
| 2008/0308607 A1 | 12/2008 | Timm et al. |
| 2009/0018535 A1 | 1/2009 | Schechter et al. |
| 2009/0112229 A1 | 4/2009 | Omori et al. |
| 2009/0131934 A1 | 5/2009 | Odom et al. |
| 2009/0182327 A1 | 7/2009 | Unger |
| 2009/0188094 A1* | 7/2009 | Cunningham ..... A61B 18/1445 29/244 |
| 2009/0312773 A1 | 12/2009 | Cabrera et al. |
| 2010/0042142 A1 | 2/2010 | Cunningham |

(56) References Cited

U.S. PATENT DOCUMENTS

| | | | |
|---|---|---|---|
| 2010/0094289 A1* | 4/2010 | Taylor | A61B 18/1445 606/52 |
| 2010/0179540 A1 | 7/2010 | Marczyk et al. | |
| 2010/0249769 A1 | 9/2010 | Nau, Jr. et al. | |
| 2011/0054468 A1 | 3/2011 | Dycus | |
| 2011/0054471 A1 | 3/2011 | Gerhardt et al. | |
| 2011/0060335 A1 | 3/2011 | Harper et al. | |
| 2011/0071523 A1 | 3/2011 | Dickhans | |
| 2011/0270245 A1 | 11/2011 | Horner et al. | |
| 2011/0270251 A1 | 11/2011 | Horner et al. | |

FOREIGN PATENT DOCUMENTS

| | | |
|---|---|---|
| DE | 2627679 A1 | 1/1977 |
| DE | 3423356 A1 | 1/1986 |
| DE | 3612646 A1 | 4/1987 |
| DE | 8712328 U1 | 2/1988 |
| DE | 4303882 C2 | 2/1995 |
| DE | 4403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 10045375 A1 | 4/2002 |
| DE | 202007009317 U1 | 8/2007 |
| DE | 102004026179 B4 | 1/2009 |
| EP | 1159926 A2 | 12/2001 |
| JP | 61501068 | 9/1984 |
| JP | 65502328 | 3/1992 |
| JP | 55106 | 1/1993 |
| JP | 540112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11070124 | 3/1999 |
| JP | 11244298 | 9/1999 |
| JP | 2000102545 A | 4/2000 |
| JP | 2000342599 A | 12/2000 |
| JP | 2000350732 A | 12/2000 |
| JP | 2001008944 | 1/2001 |
| JP | 2001029356 | 2/2001 |
| JP | 2001128990 A | 5/2001 |
| SU | 401367 A1 | 10/1973 |
| WO | 0036986 A1 | 6/2000 |
| WO | 0154604 A1 | 8/2001 |
| WO | 2005110264 A3 | 4/2006 |
| WO | 2008045348 | 4/2008 |
| WO | 2008045350 | 4/2008 |

OTHER PUBLICATIONS

Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/USO1/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report dated Mar. 4, 2016, issued in European Application No. 15195484.
European Search Report for European Application No. 11167437 dated Aug. 8, 2011.
U.S. Appl. No. 09/387,883, filed Sep. 1, 1999.
U.S. Appl. No. 09/591,328, filed Jun. 9, 2000.
U.S. Appl. No. 12/336,970, filed Dec. 17, 2008.
Michael Choti, "Abdominoperineal Resection with the LigaSure Vessel Sealing System and LigaSure Atlas 20 cm Open Instrument" Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al., "Comparison of Healing Process Following Ligation with Sutures and Bipolar Vessel Sealing" Surgical Technology International (2001).
"Electrosurgery: A Historical Overview". Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

(56) References Cited

OTHER PUBLICATIONS

Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/Product Literature 2001.
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue"; Miccai 2005; LNCS 3750 pp. 624-632, dated: 2005.
McLellan et al., "Vessel Sealing for Hemostasis During Pelvic Surgery" Int'l Federation of Gynecology and Obstetrics FIGO World Congress 2000, Washington, DC.
McLellan et al. "Vessel Seating For Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Intl Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Intl Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report-extended-EP 05021937.7 dated Mar. 15, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.

\* cited by examiner

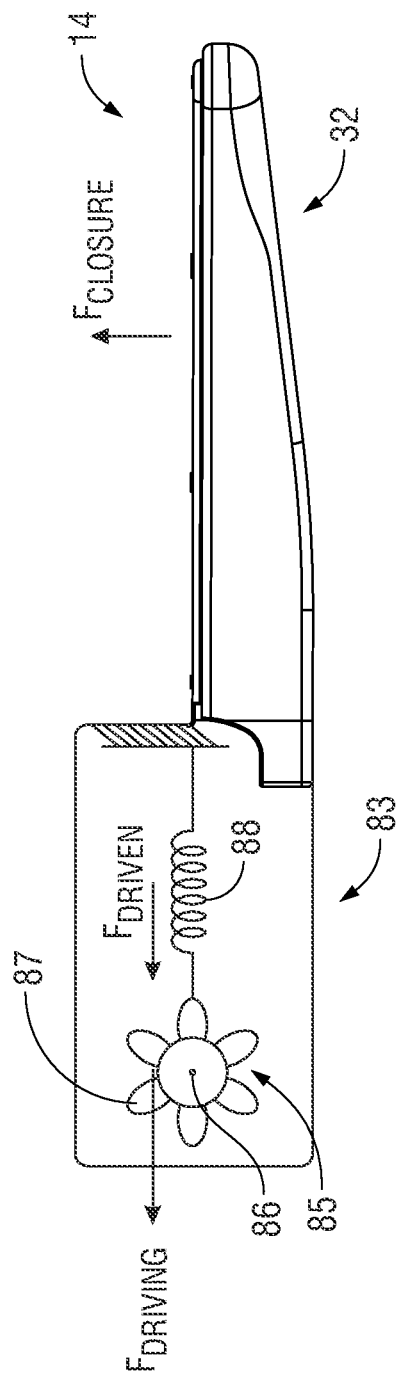
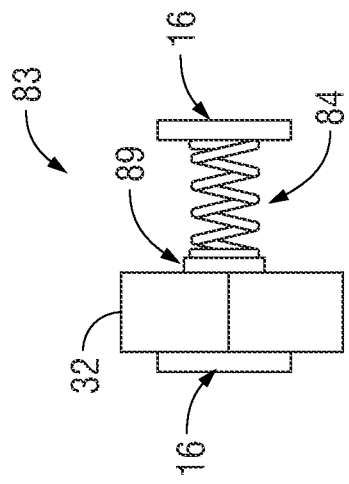
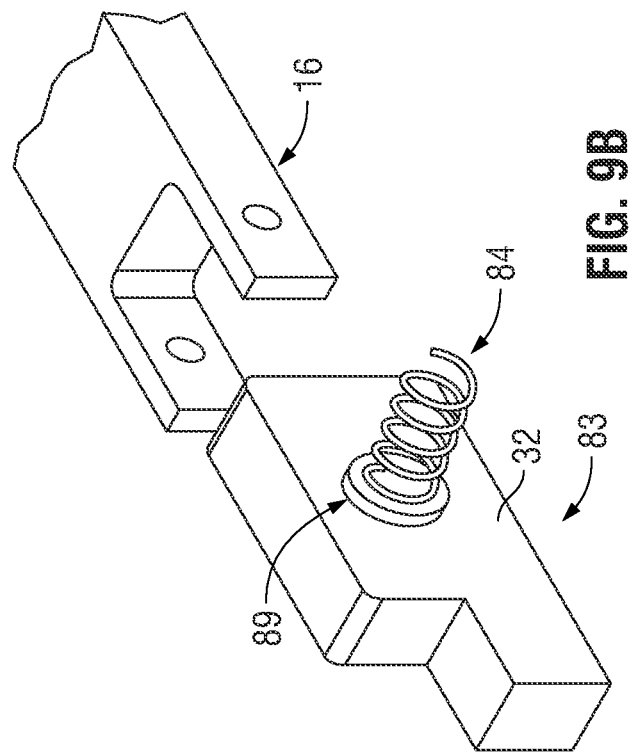
FIG. 9A
FIG. 9B
FIG. 9C

ACCURATE JAW CLOSURE FORCE IN A CATHETER BASED INSTRUMENT

CROSS-REFERENCE TO RELATED APPLICATIONS

This is a continuation of U.S. patent application Ser. No. 12/786,589, filed on May 25, 2010.

FIELD

The present disclosure relates to an apparatus for remotely activating jaw members on an articulating surgical instrument. In particular, the apparatus includes a driving mechanism for appropriately transmitting force from a proximal end to a distal end of the instrument to properly clamp tissue between the jaw members.

BACKGROUND

Typically in a laparoscopic surgical procedure, a small incision or puncture is made in a patient's body. A cannula is then inserted into a body cavity through the incision, which provides a passageway for inserting various surgical devices such as scissors, dissectors, retractors, or similar instruments. To facilitate operability through the cannula, instruments adapted for laparoscopic surgery typically include a relatively narrow shaft supporting an end effector at its distal end and a handle at its proximal end. Arranging the shaft of such an instrument through the cannula allows a surgeon to manipulate the proximal handle from outside the body to cause the distal end effector to carry out a surgical procedure at a remote internal surgical site.

An articulating laparoscopic or endoscopic instrument may provide a surgeon with a range of operability suitable for a particular surgical procedure. The instrument may be configured such that the end effector may be aligned with an axis of the instrument to facilitate insertion through a cannula, and thereafter, the end effector may be caused to articulate, pivot or move off-axis as necessary to appropriately engage tissue. When the end effector of an articulating instrument comprises a pair of jaw members for grasping tissue, such as that of electrosurgical forceps, a force transmission mechanism such as a drive wire may be provided to open or close the jaw members. For example, the drive wire may extend through the shaft of the instrument from the handle to the jaw members such that the surgeon may create a dragging force in the drive wire which pulls the drive wire proximally for a predetermined distance. The dragging force in the drive wire leads to a pulling force acting upon the jaw members to move them close to one another for a distance determined by the traveling distance of the drive wire. As a result, proximal motion of the drive wire translates into rotational motion of the jaw members. As a result, the closure or clamping force generated in the jaw members is related to the pulling force acting upon the jaw members as well as the travelling distance of the drive wire.

Instruments such as electrosurgical forceps are commonly used in open and endoscopic surgical procedures to coagulate, cauterize and seal tissue. A detailed discussion of the use of an electrosurgical forceps may be found in U.S. Pat. No. 7,255,697 to Dycus et al. Such forceps typically includes a pair of jaw members that can be controlled by a surgeon to grasp a targeted tissue. The pair of jaw members generate a significant closure force between jaw members to coagulate, cauterize or seal small diameter blood vessels, vascular bundles or any two layers of tissue with the application of electrosurgical or RF energy. The two layers may be grasped and clamped together by the jaw members, and an appropriate amount of electrosurgical energy may be applied through the jaw members. The closure force typically generated by this type of procedure may present difficulties when using a typical drive wire to open and close the jaw members of an articulating instrument.

For example, a surgeon's efforts to close the jaw members may be frustrated due to articulation of the instrument. When the instrument is in its articulated configuration, the drive wire may contact the articulated shaft of the instrument thus resulting in friction that reduces the pulling force acting upon the jaw members. Additionally, the distance that the drive wire needs to travel to completely close the jaw members in an aligned configuration differs from that in an articulated configuration.

SUMMARY

The present disclosure describes an endoscopic surgical instrument including a housing, an end effector, an elongated shaft and a driving assembly. The end effector is operable from the housing to surgically manipulate tissue. The end effector includes two opposable jaw members which are movable from an open configuration for receiving tissue therebetween to a closed configuration for manipulating tissue. The elongated shaft extends between the housing and the end effector. The elongated shaft includes a proximal portion coupled to the housing, a distal portion coupled to the end effector and an articulation joint between the proximal portion and the distal portion. The proximal portion defines a longitudinal axis. The articulation joint is adapted to move the distal portion between an aligned configuration and an articulated configuration with respect to the longitudinal axis. The driving assembly comprises a first spring in connection with a drive wire. The driving assembly is configured to induce motion in the jaw members between the open configuration and the closed configuration. The driving assembly maintains a closure pressure in the range between about 3 kg/cm$^2$ and about 16 kg/cm$^2$ between the aligned configuration and the articulated configuration of the elongated shaft.

In one embodiment, the first spring defines a spring constant dimensioned to maintain a closure pressure in the range between about 3 kg/cm2 and about 16 kg/cm2 between the aligned configuration and the articulated configuration.

In another embodiment, the driving assembly includes a clutch assembly disposed between the drive wire and the end effector. The clutch assembly includes a clutch connected to the drive wire, and a second spring disposed between the clutch and the end effector. The clutch assembly imparts a consistent closure pressure between the aligned configuration and the articulated configuration.

The driving assembly may also include a tube circumferentially surrounding the drive wire. The tube defines a plurality of spaced protrusions on an inner wall thereof. The spaced protrusions are configured to maintain the drive wire in the center of the tube during translation thereof when the elongated shaft is disposed in the articulated configuration. The spaced protrusions on the inner wall of the tube include a friction coefficient substantially less than a friction coefficient of the elongated shaft.

In a certain embodiment, the driving assembly includes a rolling mechanism. The rolling mechanism includes a roller bearing feature connected to the first spring, a control wire connected to the distal end of the elongated shaft, a lever with a first end connected to the roller bearing feature and a second end connected to the control wire, and a second spring with a first end connected to the roller bearing feature and a second end connected to the drive wire. The rolling mechanism maintains a consistent closure force between the articulated and aligned configurations.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 9A is a schematic illustration of a clutch assembly in accordance with another embodiment of the present disclosure;

FIG. 9B is a schematic illustration of a perspective view of another embodiment of the clutch assembly;

FIG. 9C is a schematic illustration of a cross-section of the clutch assembly of FIG. 9B;

DETAILED DESCRIPTION

Figure 1:
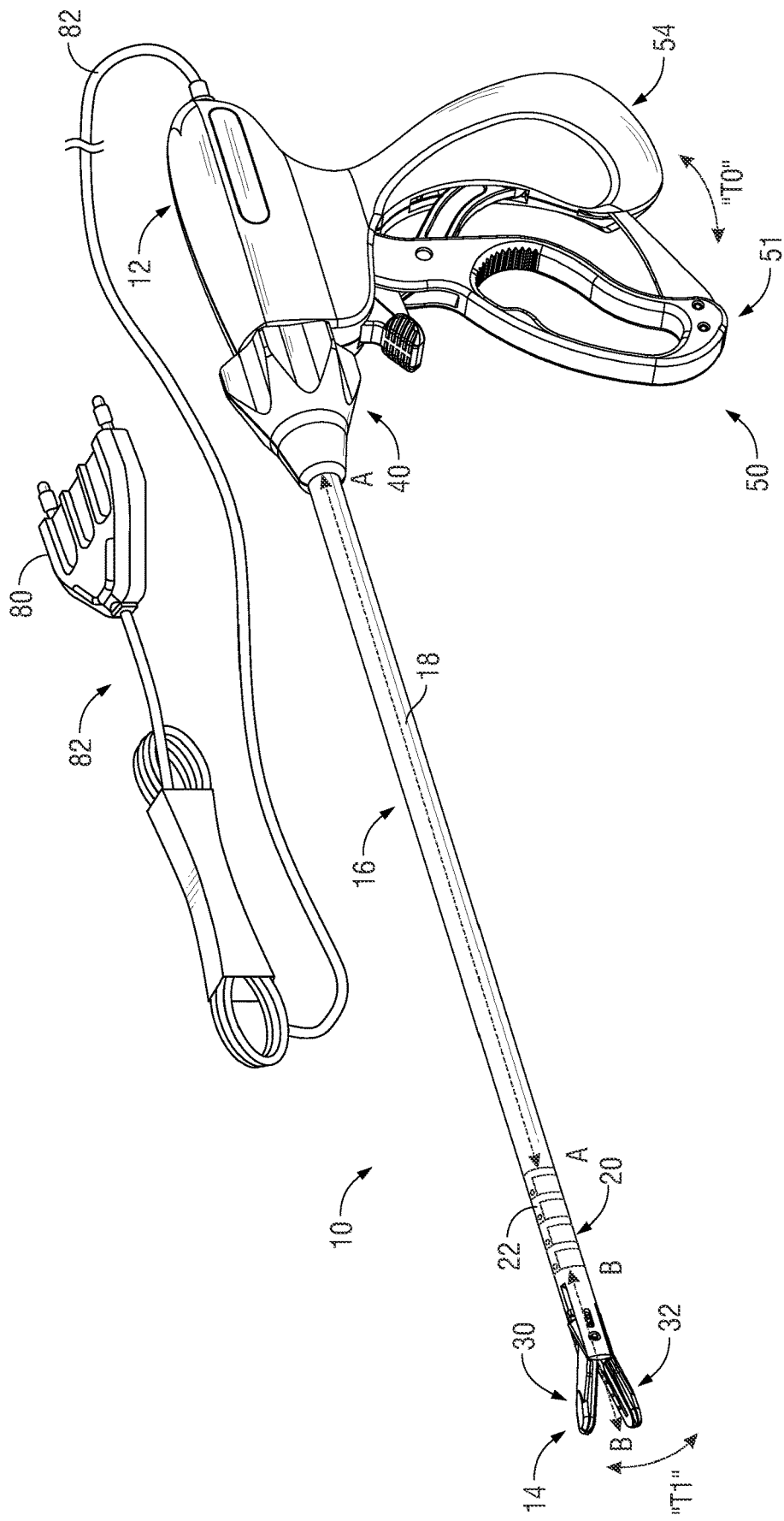
FIG. 1 is a perspective view of an articulating surgical instrument in accordance with an embodiment of the present disclosure.

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to the user and the term "distal" or "leading" refers to the end of the apparatus that is farther from the user. In the following description, well-known functions or constructions are not described in detail to avoid obscuring the present disclosure in unnecessary detail.

Referring initially to FIG. 1, an embodiment of an electrosurgical instrument is depicted generally as 10. The instrument 10 includes a housing 12 remotely supporting an end effector 14 through an elongated shaft 16.

Figure 2:
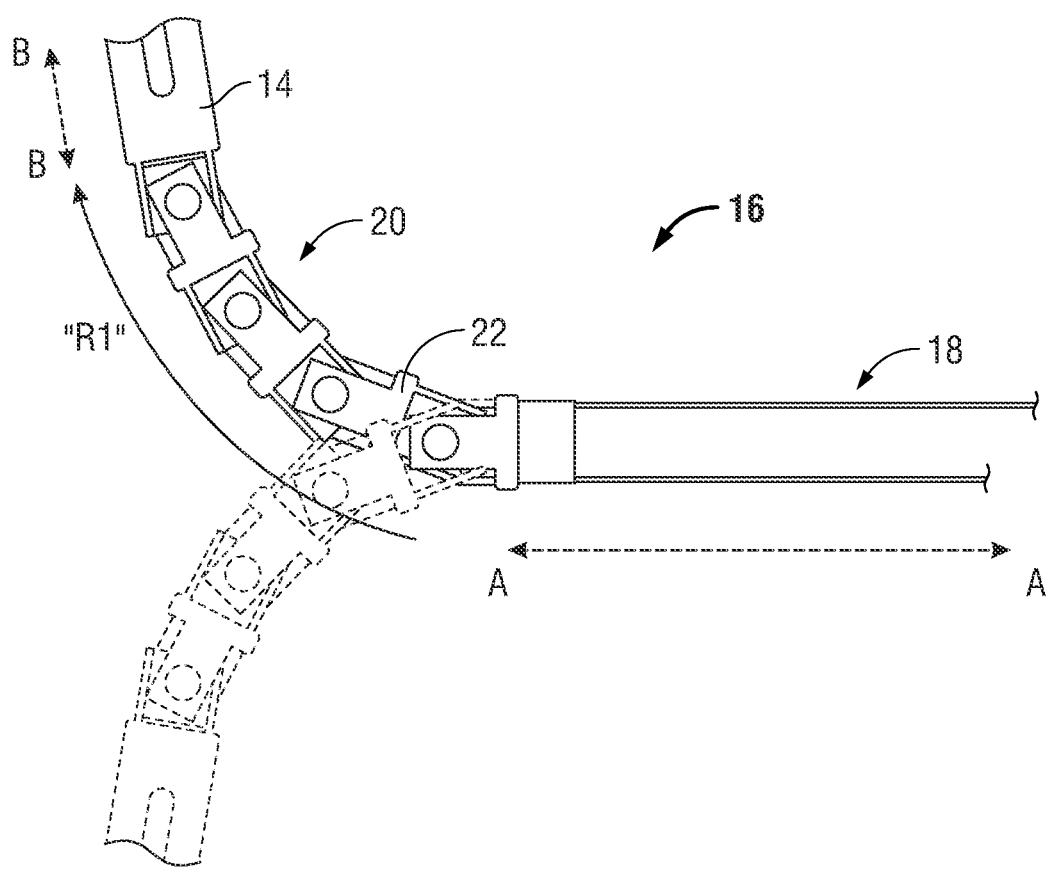
FIG. 2 is an enlarged, perspective view of a distal articulating section of the instrument of FIG. 1 in an articulated configuration.

Elongated shaft 16 includes a proximal portion 18 extending from the housing 12 and an articulating distal portion 20 supporting the end effector 14. The proximal portion 18 defines a longitudinal axis A-A, and is sufficiently long to position the end effector 14 through a cannula (not shown). The articulating distal portion 20 defines one or more joints 22 between the proximal portion 18 of the elongated shaft 16 and the end effector 14 permitting the end effector 14 to articulate or pivot relative to the longitudinal axis A-A. The end effector 14 defines an end effector axis B-B, which may be aligned with the longitudinal axis A-A to facilitate insertion of the end effector 14 through the cannula (not shown), and thereafter moved to orient the end effector 14 relative to a surgical site within the body of a patient. When the end effector axis B-B is aligned with the longitudinal axis A-A of the proximal portion 18, as illustrated in FIG. 1, the elongated shaft 16 is in an aligned configuration. By contrast, as illustrated in FIG. 2, when the end effector axis B-B is pivoted relative to the longitudinal axis A-A of the proximal portion 18 in the direction indicated by the arrow sign "R1", the elongated shaft 16 is in an articulated configuration. The elongated shaft 16 may be made of a rigid material. Alternatively, the elongated shaft 16 may be made of a flexible material, such as in a catheter-based instrument for endoluminal-type procedures.

With continued reference to FIG. 1, the end effector 14 includes a pair of opposing jaw members 30 and 32. The jaw members 30, 32 are operable from the housing 12 to move between an open configuration to receive tissue, and a closed configuration to clamp the tissue and impart an appropriate closing pressure thereto. When the end effector 14 is in the open configuration, a distal portion of each of the jaw members 30, 32 is spaced from the distal portion of the other of the jaw members 30, 32. When the end effector 14 is in the closed configuration, the distal portions of the jaw members 30, 32 are closer together. The end effector 14 is configured for bilateral movement wherein both jaw members 30 and 32 move relative to the end effector axis B-B between the open and closed configurations, as further discussed below with respect to FIG. 4. Unilateral motion is also contemplated wherein one of the jaw members 30, 32, e.g., jaw member 32 remains stationary relative to the end effector axis B-B and the other of the jaw members 30, 32, e.g., jaw member 30 is moveable relative to the end effector axis B-B, as discussed in detail below with respect to FIG. 5.

As best seen in FIG. 1, instrument 10 includes an electrical interface or plug 80 that connects the instrument 10 to a source of electrosurgical energy, e.g., a generator (not shown). An electrical cable 82 extends from the plug 80 to the housing 12 which securely connects the cable 82 to the instrument 10. The electrical cable 82 is in electrical communication with at least one of the jaw members 30, 32 such that the electrosurgical energy supplied by the generator may be delivered to tissue clamped in the end effector 14.

The housing 12 includes various actuators that are responsive to manipulation by an operator to induce these and other movements of the end effector 14. For instance, actuation of the rotation assembly 40 rotates the elongated shaft 16 which, in turn, rotates the end effector 14 in the clockwise or counter-clockwise direction to manipulate and grasp tissue. The housing 12 further includes a handle assembly 50 and a driving assembly 60, as shown in FIG. 3, which jointly impart movement of the opposing jaw members 30 and 32 relative to one another to grasp tissue therebetween.

Figure 3:
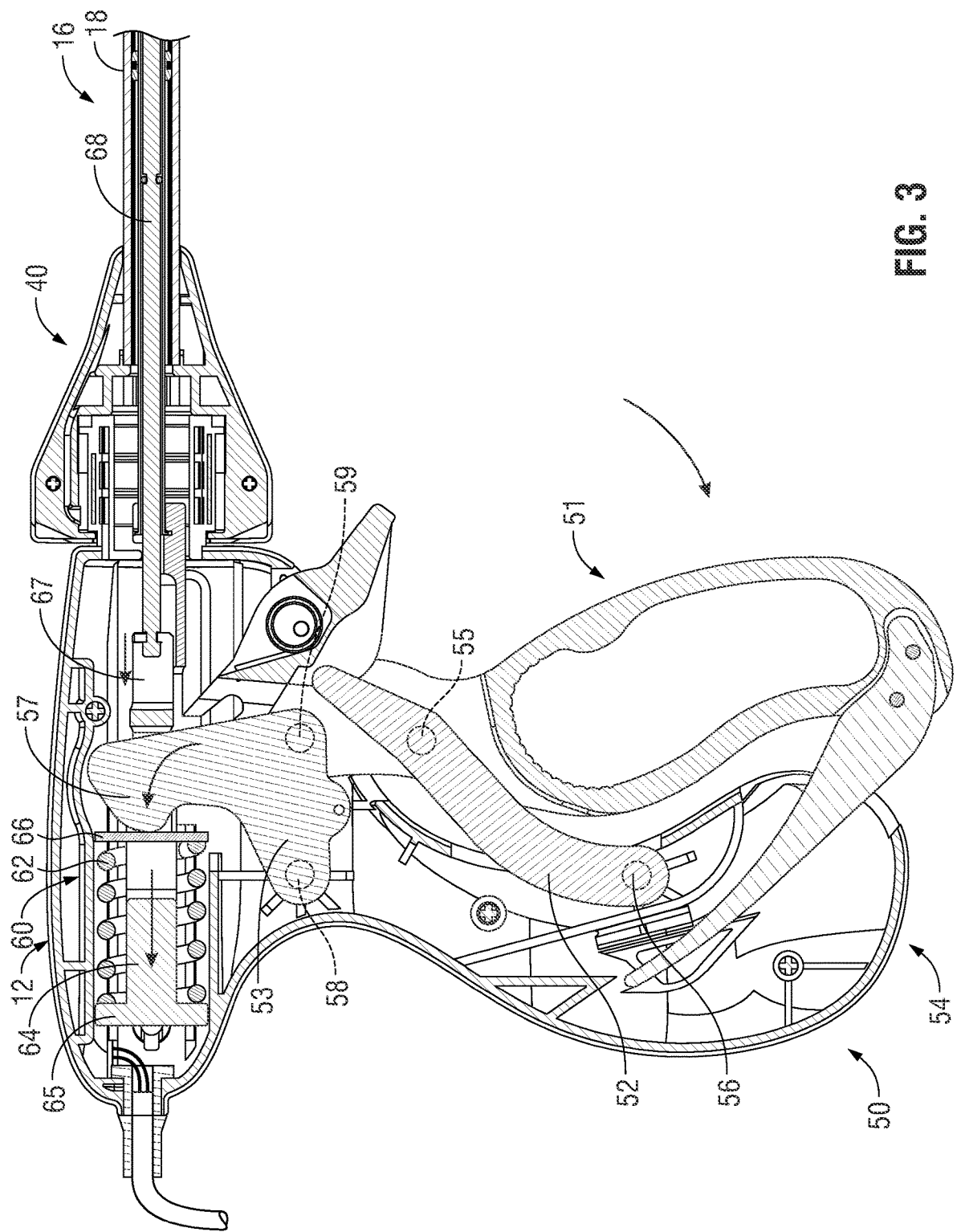
FIG. 3 is a cross-section of the articulating surgical instrument of FIG. 1 showing the internal working components thereof.

With reference to FIG. 3, the handle assembly 50 can generally be characterized as a four-bar mechanical linkage composed of the following elements: movable handle 51, a link 52, a cam-like link 53 and a base link embodied by stationary handle 54 and a pair of pivot points 55 and 56. The cam-like link 53 includes an upper cam piston 57, a fixed pivot 58 and a handle pivot 59. Although shown as a four-bar mechanical linkage, the present disclosure contemplates other linkages to effect relative motion of the jaw members 30 and 32 as is known in the art. Once actuated, movable handle 51 moves in a generally arcuate fashion towards stationary handle 54 which causes link 52 to rotate proximally about pivots 55 and 56 which, in turn, cause cam-like link 53 to rotate about pivots 58 and 59 in a generally proximal direction. Movement of the cam-like link 53 imparts movement to the driving assembly 60 as explained in more detail below.

The driving assembly 60 includes a coil spring 62 mounted atop a spring mount 64. The spring mount 64 includes a circular flange 65 at the proximal end thereof, which is dimensioned to bias the proximal end of the coil spring 62 once the spring 62 is seated within the housing 12. The distal end of the spring mount 64 has a compression tab 66 dimensioned to bias the distal end of the coil spring 62. Once assembled, the spring 62 is poised for compression atop the spring mount 64 upon actuation of the handle assembly 50. The driving assembly 60 further includes a compression sleeve 67 which is slidingly disposed within the spring mount 64, and a drive wire 68 that extends through the elongated shaft 16 connecting between the end effector 14 and the housing 12. The distal end of the compression sleeve 67 engages the proximal end of the drive wire 68 such that proximal movement of the compression sleeve 67 actuates the drive wire 68 in a proximal direction. Proximal movement of the drive wire 68 closes jaw members 30 and 32 about tissue, as explained further below with respect to FIGS. 4 and 5.

As best seen in FIG. 3, cam piston 57 is poised in abutting relationship with the compression tab 66 such that movement of the handle assembly 50 rotates cam piston 57 proximally against coil spring 62. More particularly, movement of the cam piston 57 via movement of the handle assembly 50 moves the compression tab 66 proximally, which, in turn, compresses the coil spring 62, and actuates the compression sleeve 67 to move proximally. Proximal motion of the compression sleeve 67 translates into proximal motion of the drive wire 68, which, in turn, translates into rotational motion of the jaw members 30 and 32. A more complete description of an instrument having a handle assembly and a driving assembly that impart proximal movement of a drive wire can be found in U.S. Pat. No. 7,083,618 to Couture et al. (hereinafter "Couture '618' patent").

Figure 4:
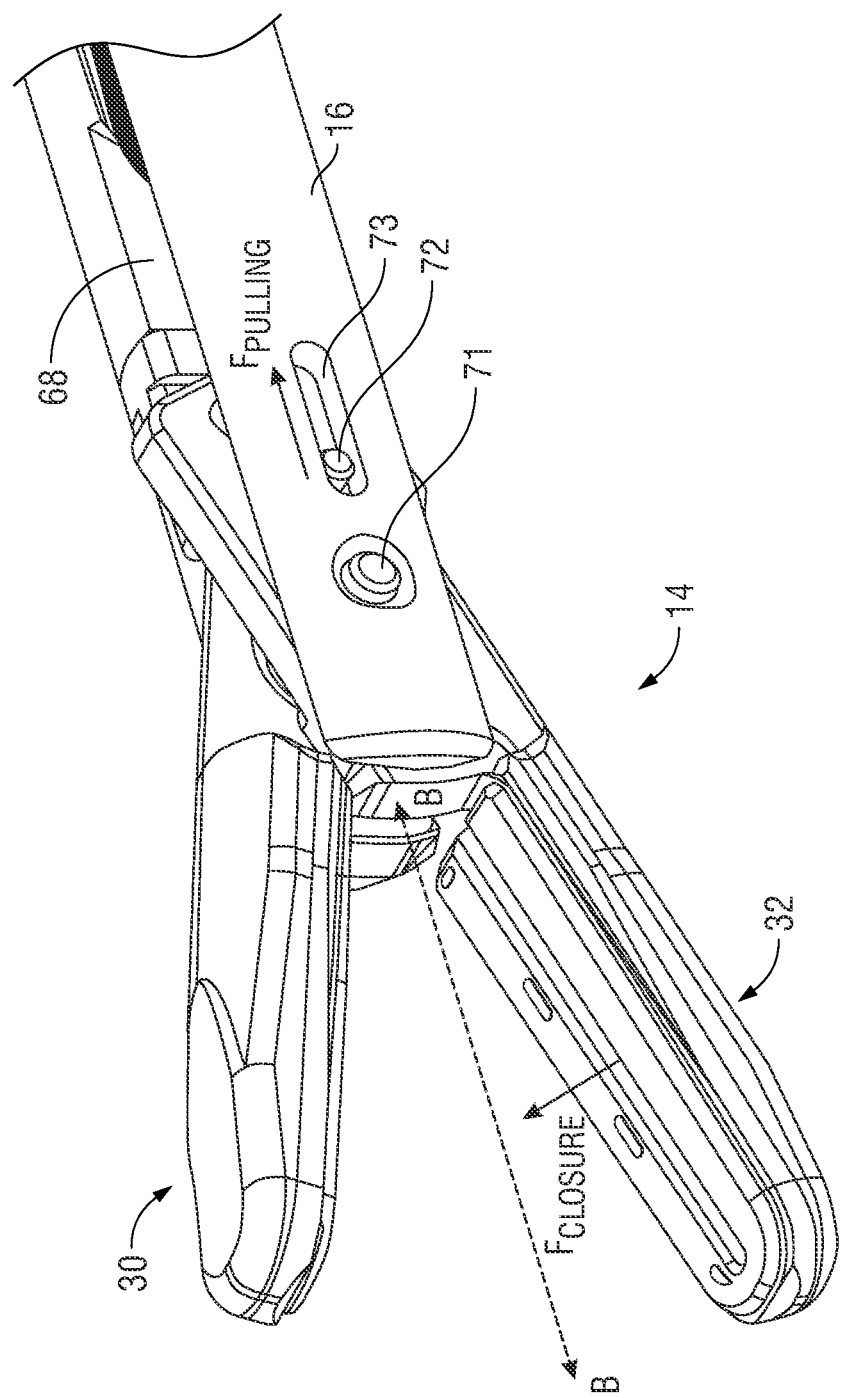
FIG. 4 is a perspective view of an end effector of one embodiment of the surgical instrument configured for bilateral movement.

In an example in which the end effector 14 is configured for bilateral movement, as illustrated in FIG. 4, the jaw members 30 and 32 are secured to the elongated shaft 16 through a pivot pin 71. Each of the jaw members defines a cam slot (obstructed from view in FIG. 4) having a common cam pin 72 disposed therethrough. The cam pin 72 is configured to ride along the cam slots and a longitudinal slot 73 defined on the elongated shaft 16. Longitudinal reciprocation of the cam pin 72 through the cam slots and the longitudinal slot 73 rotates jaw members 30 and 32 about the pivot pin 71 between the open and closed configurations. The distal end of the drive wire 68 defines a pin slot (not shown) dimensioned to house the cam pin 72 such that longitudinal reciprocation of the drive wire 68 translates the cam pin 72 along the cam slots and the longitudinal slot 73, which, in turn, rotates the jaw members 30 and 32 about the pivot pin 71. More specifically, proximal motion of the drive wire 68 induces the jaw members 30 and 32 to a closed configuration, whereas distal motion of the drive wire 68 induces the jaw members 30 and 32 to an open configuration. A more complete description of an instrument having an end effector configured for bilateral movement can be found in the Couture '618 patent.

Figure 5:
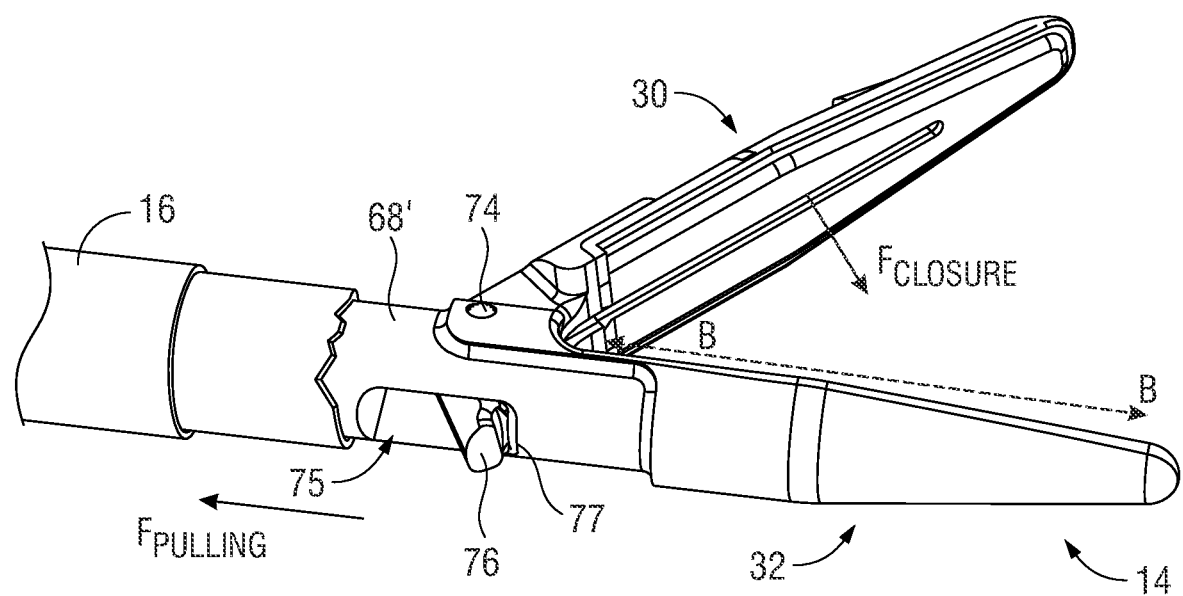
FIG. 5 is a perspective view of an end effector of another embodiment of the surgical instrument configured for unilateral movement.

In another example in which the end effector 14 is configured for unilateral movement, as illustrated in FIG. 5, the jaw member 32 is fixed relative to the shaft 16, whereas the other jaw member 30 pivots about a pivot pin 74 to grasp tissue. The pivoting jaw member 30 includes a detent or protrusion 76 which extends from the jaw member 30 through a longitudinal slot 75 disposed within the drive sleeve 68'. The pivoting jaw member 30 is actuated by sliding the drive sleeve 68' axially within the shaft 16 such that a distal end 77 of the longitudinal slot 75 abuts against the detent 76 on the pivoting jaw member 30. Proximal motion of the drive sleeve 68' closes the jaw members 30 and 32 about the tissue grasped therebetween, whereas distal motion of the drive sleeve 68' opens the jaw members 30 and 32. A more complete description of an instrument having an end effector configured for unilateral movement can be found in U.S. Pat. No. 7,156,846 to Dycus et al.

Based on the above configuration, movement of the movable handle 51 activates the four-bar linkage which, in turn, actuates the driving assembly 60, and subsequently the jaw members 30 and 32. More specifically, as the movable handle 51 is squeezed, the cam-like link 53, through the mechanical advantage of the four-bar mechanical linkage, is rotated generally proximally about pivot points 58 and 59 such that the cam piston 57 biases compression tab 66 which compresses the spring 62 against the circular flange 65 of the spring mount 64. Simultaneously, the drive wire 68 (or drive sleeve 68') is pulled proximally by the compression sleeve 67 which, in turn, closes the jaw members 30 and 32 relative to one another, as explained above with respect to FIGS. 4-5. As illustrated in FIG. 1, motion of the movable handle 51 in the direction of arrows "T0" induces motion in the jaw members 30 and 32 in the direction of arrow "T1" from the open configuration to the closed configuration. On the other hand, separation of the movable handle 51 from the stationary handle 54 moves the jaw members 30, 32 from the closed configuration to the open configuration.

Figure 6A:
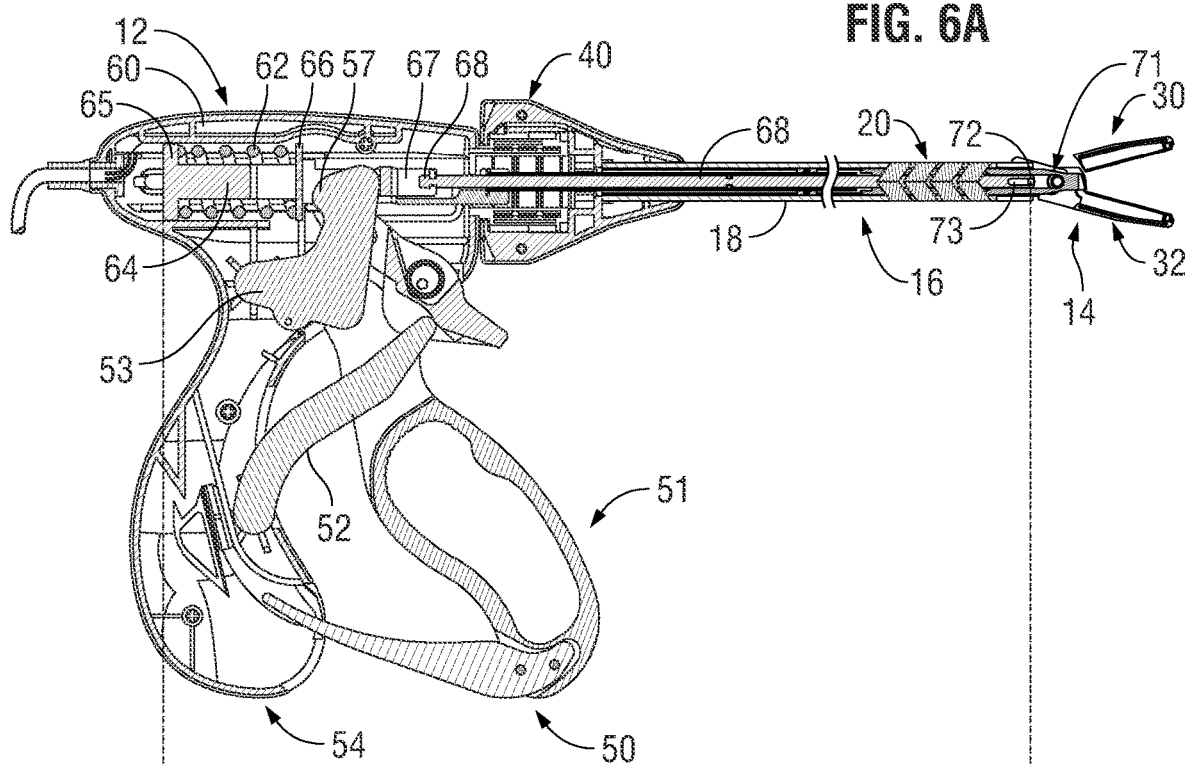
FIG. 6A is cross-section of the articulating surgical instrument of FIG. 1 showing the end effector in an open configuration.
Figure 6B:
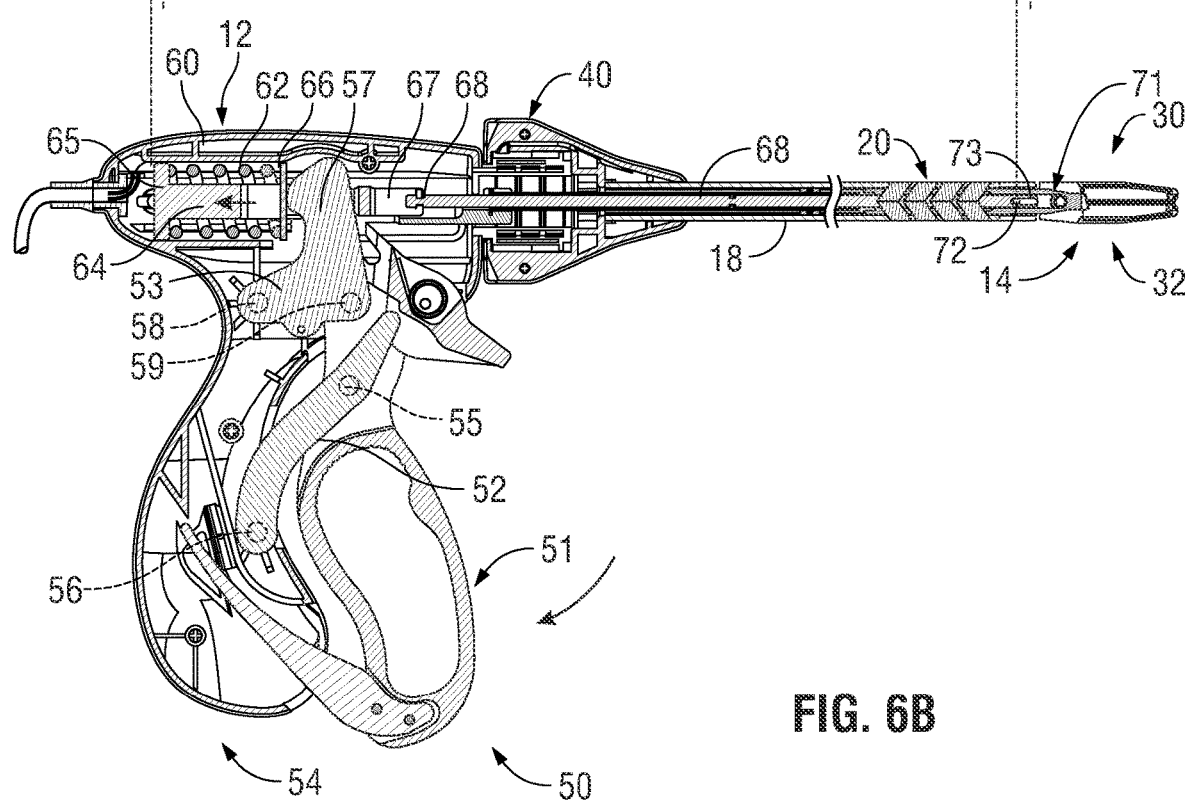
FIG. 6B is a cross-section of the articulating surgical instrument of FIG. 1 showing the end effector in a closed configuration.

The handle assembly 50 enables the user to selectively compress the coil spring 62 for a specific distance $\Delta y$ which, in turn, pushes the circular flange 65 proximally for a distance $\Delta y$, as illustrated in FIGS. 6A-B. Proximal motion of the circular flange 65 results in proximal motion of the spring mount 64, which, in turn, results in proximal motion of the compression sleeve 67, and consequently results in proximal motion of the drive wire 68 (or drive sleeve 68', referred to hereinafter for simplicity as drive wire 68) a distance $\Delta y$. The proximal motion of the drive wire 68 translates into longitudinal motion of the cam pin 72 a distance $\Delta y$ along the longitudinal slot 73 in the proximal direction, as illustrated in FIGS. 6A-B. As shown in FIGS.

6A-B, when the distance Δy corresponds to the length of the longitudinal slot 73, the compression of the spring 62 causes the cam pin 72 to travel the entire length of the longitudinal slot 73, thereby completely closing the jaw members. Further, the compression of the spring 62 imparts a specific load on the drive wire 68. As illustrated in FIG. 4, the specific load on the drive wire 68 ultimately becomes a pulling force Fpulling acting upon the cam pin 72 to drive the pin 72 proximally. The specific load on the drive wire 68 is also converted to a closure force Fclosure exerted by the jaw members 30 and 32 about the jaw pivot 71 by way of cam pins 72. Similarly, with respect to FIG. 5, the specific load on the drive sleeve 68' becomes a pulling force Fpulling acting upon the detent 76 to cause it to move proximally. The load on the drive sleeve 68' is also converted to a closure force Fclosure exerted by the jaw members 30 and 32 about the pivot pin 74 by way of the detent 76. Thus, regardless of whether the end effector 14 is configured for bilateral or unilateral motion, proximal motion of the drive wire 68 of a distance Δy can translate into rotational motion of the opposing jaw members 30 and 32 from an open configuration to a closed configuration and simultaneously transmit a specific closure force to the opposing jaw members 30 and 32.

To effectively clamp tissue between the jaw members 30 and 32, a relatively high clamping force is typically generated to impart a closure pressure on the tissue in a desirable range of from about 3 kg/cm2 to about 16 kg/cm2. The closure pressure is determined by two factors: (1) whether jaw members 30 and 32 are in a closed configuration and (2) the closure force exerted by the jaw members 30 and 32. As explained above, both factors are determined by the proximal motion of the drive wire 68, which is ultimately determined by the compression of the coil spring 62 through the handle assembly 50. In the prior art, the closure pressure within the particularly desirable range can be readily achieved when the articulating instrument is in an aligned configuration, that is when the drive wire 68, the articulating distal portion 20 of the elongated shaft 16 and the end effector 14 are aligned along the same axis, as depicted in FIGS. 6A-B.

Figure 7A:
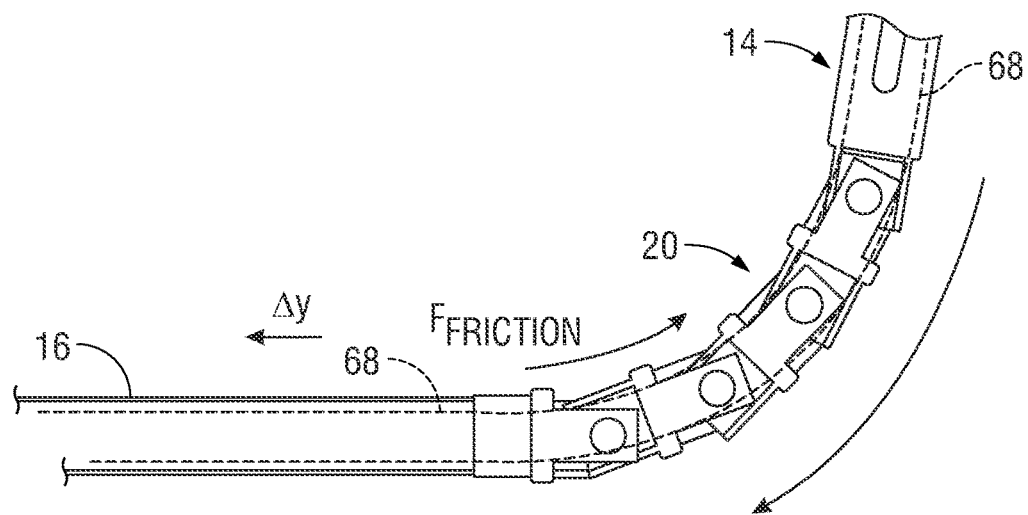
FIG. 7A is an enlarged, perspective view of a prior art distal articulating section of the instrument of FIG. 1 during proximal motion of a drive wire.
Figure 7B:
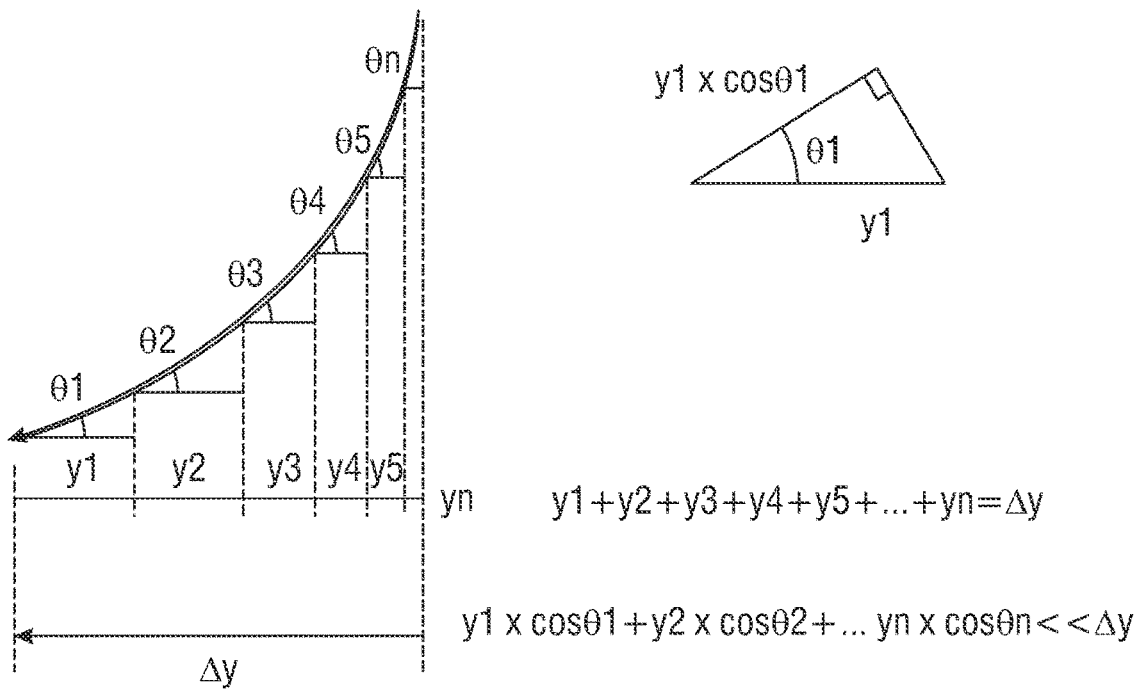
FIG. 7B is a schematic illustration of an articulated path approximated by divided components of a linear path.

However, in the prior art, when the articulating instrument is in an articulated configuration as depicted in FIG. 7A, compression of the coil spring 62 a distance Δy can no longer yield the desired closure pressure. Due to the articulation, linear motion of a distance Δy translates into curved motion of a newly defined distance Δy' along the articulated path. As shown in FIG. 7B, a linear displacement Δy can be broken down to an infinite number of linear segments y1, y2, y3, ... yi ... yn, such that Δy is defined by the following equation:

$$\Delta y = y_1 + y_2 + y_3 + \ldots + y_i + \ldots + y_n$$

Each linear segment yi comprises a divided component that represents a tangent to the articulated path. The articulated path can be approximated by its infinite number of tangent segments connecting each other. Therefore, the sum of all the divided components of the linear segments $y_1, y_2, y_3, \ldots y_i \ldots y_n$ approximates the newly defined distance Δy' along the articulated path. As shown in FIG. 7B, each divided component forms an angle $\theta_i$ with respect to the linear axis, thus each linear displacement yi corresponds to a displacement of $y_i \times \cos \theta_i$ along the articulated path. Thus, the newly defined displacement Δy' along the articulated path is defined by the following equation:

$$\Delta y' = y_1 \cdot \cos \theta_1 + y_2 \cdot \cos \theta_2 + y_3 \cdot \cos \theta_3 + \ldots + y_i \cdot \cos \theta_i + \ldots + y_n \cdot \cos \theta_n$$

Therefore, curved motion of Δy' along the articulated path is much less than proximal motion of Δy along a linear path. As a result, in the prior art, proximal motion of the drive wire 68 for a distance of Δy ultimately translates into motion of the cam pin 72 for a distance of Δy' along the longitudinal slot 73 as in a bilateral end effector as shown in FIG. 4, or translates into motion of the detent 76 for a distance of Δy' along the longitudinal 75 as in a unilateral end effector as shown in FIG. 5. In both cases, jaw members 30 and 32 can no longer be completely closed or closed under the proper closing pressure. Rather, when the instrument 10 is in an articulated configuration, compression of the spring 62 would rotate the jaw members 30 and 32 to a position less than required to generate the proper closing pressure, resulting in a closure pressure significantly below the above-identified desirable range.

Further, in the prior art, when the instrument 10 is in an articulated configuration as depicted in FIG. 7A, the drive wire 68 experiences friction $F_{friction}$ as the drive wire 68 contacts surfaces within the articulating distal portion 20, which reduces the load carried by the drive wire 68. Ultimately, the closure force $F_{closure}$ exerted by the jaw members 30 and 32 in an articulated configuration is substantially less than that in an aligned configuration. For the same reason, the closure pressure is significantly below the desirable range.

Still further, in the articulated configuration, when the jaw members 30 and 32 can hardly be closed, the surgeon may tend to apply an overly excessive amount of force on the handle 51. However, any over-compression of the handle 51 may lead to an over-compression of the coil spring 62 which imparts an overload on the drive wire 68, and which may result in an excessive rotation of the jaw members 30 and 32 relative to each other and an excessive increased closure force, eventually resulting in a closure pressure exceeding the desirable range.

The present disclosure provides solutions to compensate for the loss or increase of distance and closure force caused by the articulated path, thereby maintaining a consistent closure pressure within the desirable range between an aligned configuration and an articulated configuration.

Figure 8A:
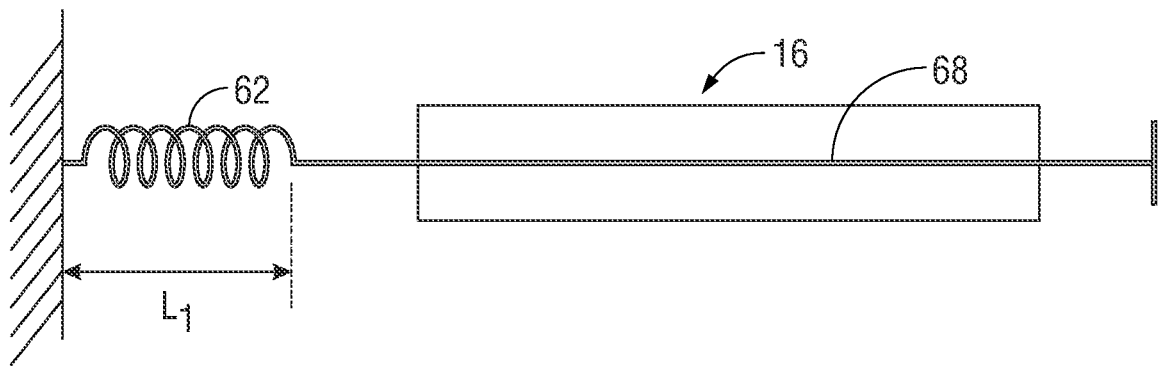
FIGS. 8A-B are schematic illustrations of a spring in connection with the drive wire in accordance with one embodiment of the present disclosure.
Figure 8B:
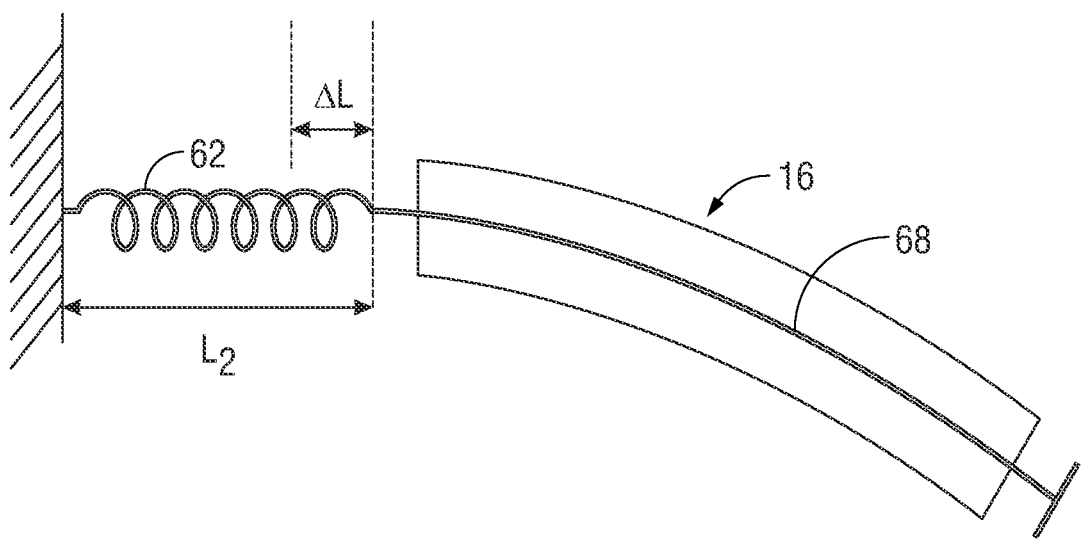

In the first embodiment, as illustrated schematically in FIGS. 8A-8B, the coil spring 62 has a spring constant such that the coil spring 62 can be stretched for a distance $\Delta L = L_2 - L_1$ as the instrument 10 is articulated upon application of force through the movable handle 51. The distance ΔL compensates for the loss of displacement due to articulation. In one example, the distance ΔL corresponds to the difference between Δy and Δy'. Based on this configuration, the drive wire 68 is induced to move proximally for an additional distance ΔL, thereby enabling the cam pin 72 of FIG. 4 or the detent 76 of FIG. 5 to travel across the full length of the longitudinal slot 73 of FIG. 4 or the longitudinal slot 75 of FIG. 5 in an articulated configuration, thereby allowing the jaw members 30 and 32 to reach a completely closed configuration under the appropriate pressure. The spring constant is also designed to provide an additional load on the drive wire 68, during proximal motion of the drive wire 68, thereby compensating the loss of load due to friction at the contact surfaces between the drive wire 68 and the articulating distal section 20 of the shaft 16, when the instrument 10 is in an articulated configuration. Thus, a consistent closure pressure within the desirable range between about 3 kg/cm2 and about 16 kg/cm2 can be maintained from an aligned configuration to an articulated configuration.

In another embodiment, as illustrated schematically in FIG. 9A, the driving assembly 60 includes a clutch assembly 83 disposed between the drive wire 68 and the jaw members 30 and 32. The clutch assembly 83 includes a clutch 85 and a spring 88. The clutch 85 may be either an analog clutch or a discrete clutch. The clutch 85 is securely attached to the end effector 14 through a rotational pivot 86. When the drive wire 68 engages in proximal motion, any load on the drive wire 68 imparts a driving force Fdriving acting upon the clutch 85. The clutch 85 slips about the rotational pivot 86 when the driving force Fdriving is beyond a certain predetermined value. During slippage of the clutch 85, the driving force Fdriving converts to a driven force Fdriven acting upon the spring 88, which distally connects to one of the plurality of clutch teeth 87. The clutch 85 is configured to have a design ratio such that any driving force Fdriving beyond a certain predetermined value imparts a driven force Fdriven within a particular range considerably less than Fdriving. The driven force Fdriven within the particular range causes the spring 88 to stretch in the proximal direction for a predetermined distance, which, in turn, induces a constant closure force on the jaw members 30 and 32. The predetermined distance corresponds to the length of the longitudinal slot 73 that the cam pin 72 needs to travel, as in a bilateral configuration illustrated in FIG. 4, or corresponds to the length of the longitudinal slot 75 that the detent 76 needs to travel as in a unilateral configuration illustrated in FIG. 5, in order to move jaw members 30 and 32 from an open configuration to a closed configuration. Thus, the clutch assembly 83 offloads any increase in force delivered by the drive wire 68 due to over-compression of the spring 62, thereby ultimately creating a constant closure force on the jaw members 30 and 32. Additionally, any excessive displacement by the drive wire 68 in the proximal direction due to over-compression is also reduced by the clutch assembly 83, avoiding excessive rotation of the jaw members 30 and 32 relative to each other. As a result, the clutch assembly 83 ensures that the closure pressure upon the tissue clamped between the jaw members 30 and 32 is maintained within the desirable range 3 kg/cm2 and about 16 kg/cm2 all time.

FIGS. 9B-9C together illustrate another embodiment of the clutch assembly 83, where the clutch assembly 83 includes a torsion spring 84 and a friction plate 89 securely attached to a jaw member 30 or 32. Unlike the clutch assembly 83 illustrated in FIG. 9A which has elements arranged in a linear fashion proximal to the jaw member 32, the friction plate 89 and the torsion spring 84 are laterally placed within respect to the jaw member 32, as clearly shown in the cross-section view of the clutch assembly 83 illustrated in FIG. 9C. Thus, by taking advantage of the lateral space on the side of the jaw member 32 to store the clutch assembly 83, this particular embodiment uses less physical space. Here, the torsion spring 84 is a spring that works by torsion or twisting, such that it stores mechanical energy when it is twisted. The amount of force or torque the torsion spring 84 exerts is proportional to the amount it is twisted. Similar to the clutch 85 discussed immediately above, the frictional plate 89 is designed to slip to overcome any increase in force delivered by the drive wire 68, which, in turn, causes the spring 84 to twist or untwist for a predetermined distance, ultimately inducing a constant closure force on the jaw members 30 and 32. In a preferred embodiment, the frictional plate 89 is designed to slip resulting in a closure pressure of 120 psi, which approximates to 8.437 kg/cm2.

Figure 10:
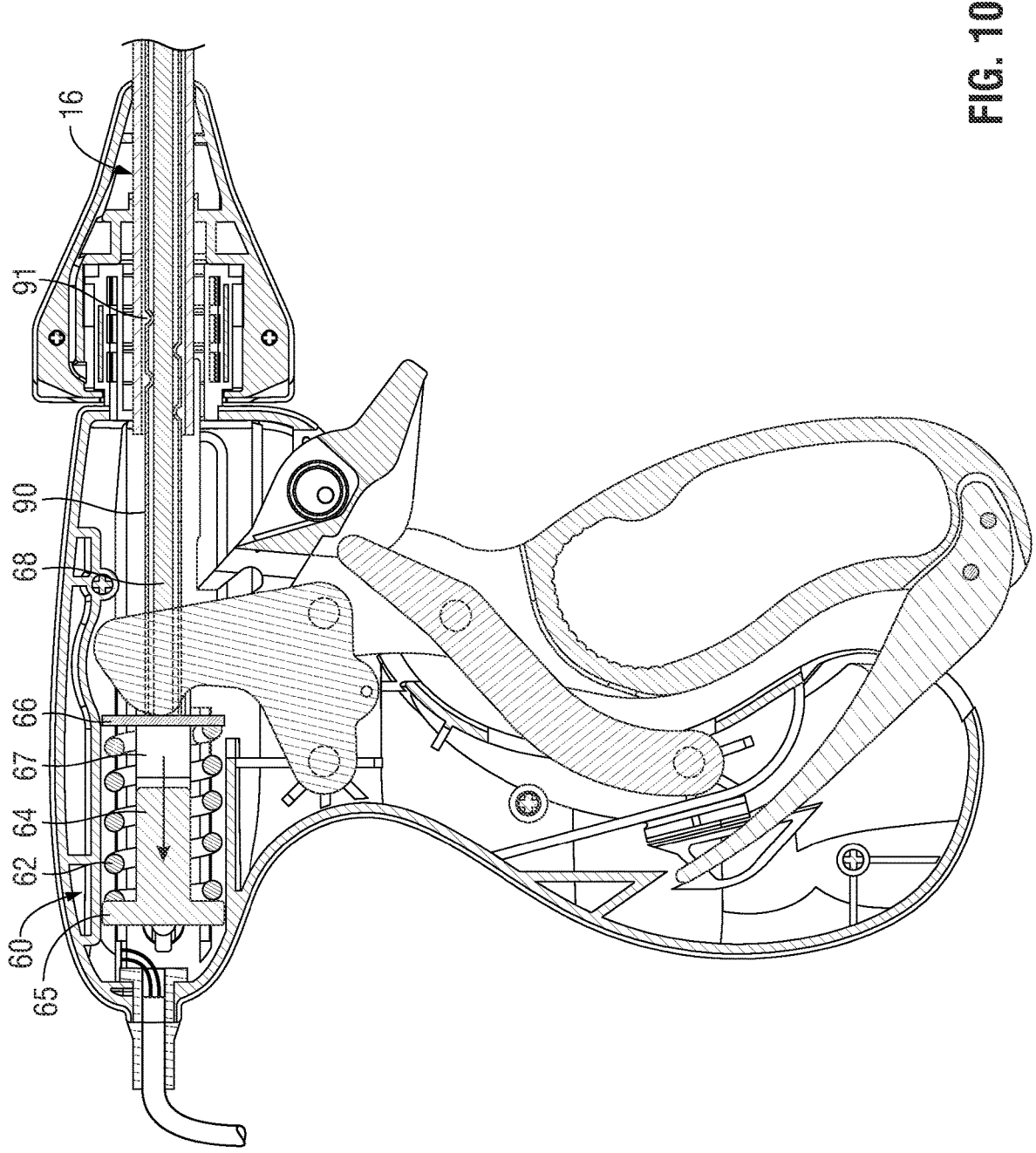
FIG. 10 is a schematic illustration of a tube circumferentially surrounding the drive wire in accordance with another embodiment of the present disclosure.

FIG. 10 shows another embodiment of the present disclosure for compensation for the increased or decreased forces on the drive wire during articulation. More particularly, the driving assembly 60 may include a tube 90 extending along the length of the elongated shaft 16, circumferentially surrounding the drive wire 68. The tube 90 serves as an intermediate layer between the elongated shaft 16 and the drive wire 68. The tube 90 is made of a material that defines a friction coefficient substantially less than that of the elongated shaft 16, resulting in an almost negligible friction between an inner surface of the tube 90 and the drive wire 68 when they are in motion. When the instrument 10 is in the articulated configuration, the tube 90 prevents direct contact between the drive wire 68 and the elongated shaft 16 that otherwise would occur in the prior art. Additionally, the tube 90 defines a plurality of spaced protrusions 91 on an inner wall thereof that protrude inwardly towards the drive wire 68. The protrusions 91 reduce the contact area between the tube 90 and the drive wire 68 to a minimal degree, thus substantially reducing any contact friction that would be experienced by the drive wire 68 during translation. Further, when the instrument 10 is articulated, the protrusions 91 maintain the drive wire 68 in the center of the tube 90 during translation thereof. Due to the physical characteristics of the tube 90, the loss of load on the drive wire 68 due to friction is significantly minimized. As such, the closure force Fclosure ultimately exerted by the jaw members 30 and 32 is maximized. The tube 90 feature may be implemented in conjunction with the spring feature as discussed in the first embodiment, such that they jointly compensate for the loss of displacement and the loss of load experienced by the jaw members due to articulation of the instrument.

Figure 11A:
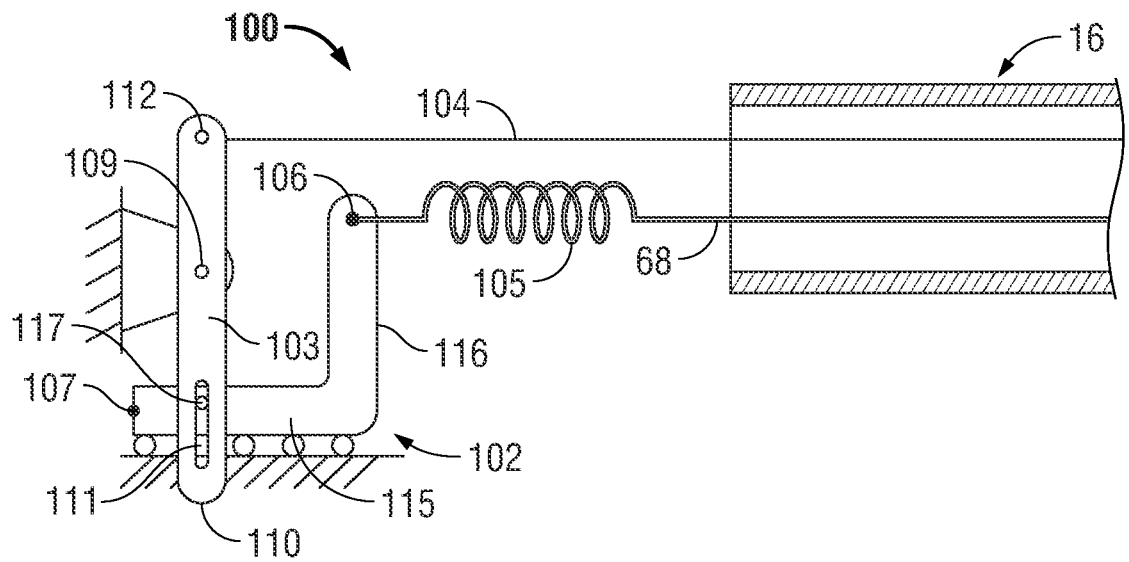
FIG. 11A is a schematic illustration of a rolling mechanism in connection with the drive wire in an aligned configuration in accordance with another embodiment of the present disclosure.
Figure 11B:
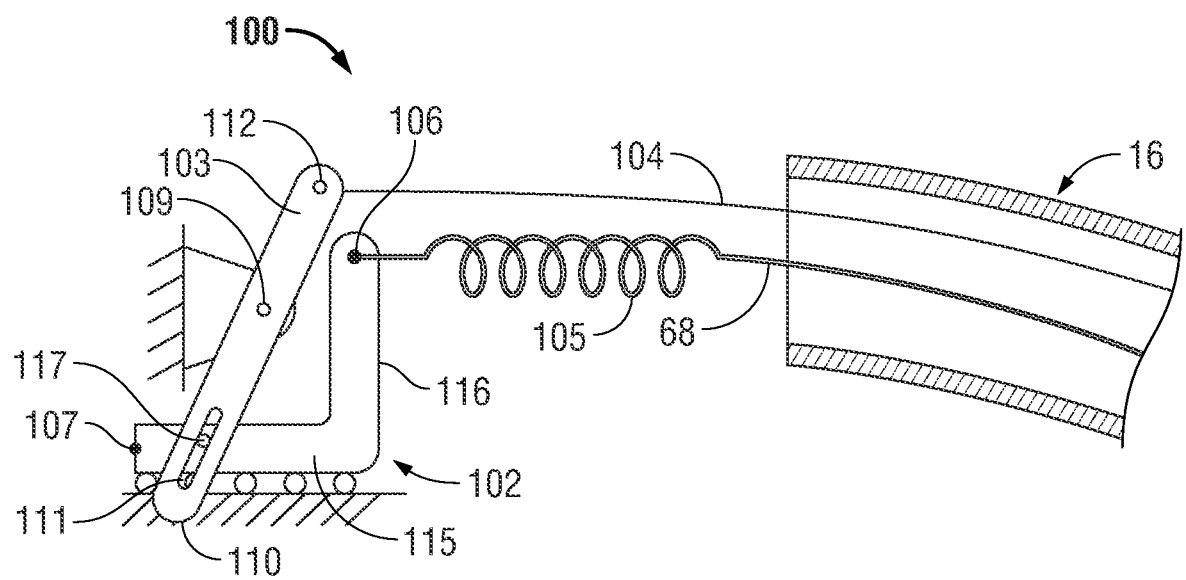
FIG. 11B is a schematic illustration of the rolling mechanism of FIG. 11A in an articulated configuration.

Another embodiment of the present disclosure is shown in FIGS. 11A-B, wherein the driving assembly 60 may further include a rolling mechanism 100 disposed between the spring 62 and the drive wire 68. The rolling mechanism 100 includes a roller bearing feature 102, a pivot link or lever 103, a flexible control wire 104, and a spring 105. The roller bearing feature 102 has two structures 115 and 116 perpendicular with respect to each other. The horizontal structure 115 has a proximal end 107 connected to the spring 62 (not shown). The vertical structure 116 defines a top end 106 fixedly connected to the spring 105. The pivot link 103 is securely connected to the housing 12 at a pivot point 109. The pivot link 103 defines a top end 112 connected to the flexible control wire 104 and a bottom end 110 reciprocally engaged with the roller bearing feature 102. Specifically, the pivot link 103 defines a longitudinal slot 111 which is configured to allow a slidable engagement with a cam pin 117 of the roller bearing feature 102, such that the cam pin 117 may slide across the longitudinal slot 111. Based on this configuration, rotation movement of the pivot link 103 may impart and/or inhibit proximal movement of the roller bearing feature 102. The flexible control wire 104 connects between the top end 112 of the pivot link 103 and the distal end of the shaft 16.

When the elongated shaft 16 is in an articulated configuration as shown in FIG. 11B, compression of the spring 62 (not shown) translates into proximal motion of the roller bearing feature 102, which, in turn, stretches the spring 105 proximally and simultaneously results in proximal motion of the drive wire 68. The expansion of the spring 105 provides additional proximal displacement to the cam pin 72 shown FIG. 4 or the detent 76 shown in FIG. 5 that compensates for the loss of displacement due to articulation. Further, the force exerted by the spring 105 due to expansion provides an additional load on the drive wire 68 which compensates for the loss of load caused by friction at the contact surfaces between the drive wire 68 and the elongated shaft 16 in the articulated configuration.

When the elongated shaft 16 is articulated, the flexible control wire 104 is under tension exerting a force on the distal end 112 of the pivot link 103, which, in turn, causes the pivot link 103 to pivot about the fixed pivot point 109 in a clockwise direction as illustrated in FIG. 11B. Because the distance defined between the fixed pivot point 109 and the top end 112 is much less than the distance defined between the fixed pivot point 109 and the bottom end 110, one small clockwise rotation at the top end 112 results in a relatively large proximal movement at the bottom end 110. As the pivot link 103 rotates in the clockwise direction, the longitudinal slot 111 of the pivot link 103 induces proximal movement of the cam pin 117, which, in turn, facilitates proximal movement of the roller bearing feature 102. Due to the reciprocal relationship between the pivot link 103 and the roller bearing feature 102, when the pivot link 103 cannot rotate any further, the cam pin 117 then reaches its proximal-most position, preventing further proximal movement of the roller bearing feature 102. In short, the pivot link 103 through its engagement with the roller bearing feature 102, facilitates proximal movement of the roller bearing feature 102, however, it also prevents the roller bearing feature 102 from any further proximal movement once the roller bearing feature 102 moved proximally for a predefined distance. Thus, the pivot link 103 and the flexible control wire 104 together prevent the spring 105 from over stretching due to over-compression of the spring 102. This configuration ensures that the closure pressure is always maintained within the desirable range between about 3 kg/cm2 and 16 kg/cm2 between the aligned configuration and the articulated configuration. Further, this particular embodiment allows a better spring design, and provides mechanisms to compensate for more frictional losses.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An apparatus for remotely activating an end effector of an articulating surgical instrument, the apparatus comprising:
   a housing including at least one actuator configured to receive an input for remotely activating an end effector of an articulating surgical instrument; and
   a driving assembly disposed within the housing, the driving assembly including a spring configured to be compressed in response to the least one actuator receiving the input to cause a drive wire to activate the end effector, the driving assembly including a compression tab and a cam piston configured to move the compression tab proximally to compress the spring, wherein the spring stretches as a result of the end effector being disposed in an articulated position thereby placing the drive wire under increased tension as a result of a spring force on the stretched spring.

2. The apparatus according to claim 1, wherein the compression tab is disposed distal to the spring and configured to bias a distal end of the spring.

3. The apparatus according to claim 1, wherein compression of the spring causes the drive wire to activate the end effector.

4. The apparatus according to claim 1, wherein compression of the spring causes the drive wire to move a cam pin through a cam slot disposed through at least one jaw member of the end effector for activating the end effector.

5. The apparatus according to claim 1, wherein the compression tab includes a distal surface and an opposing proximal surface in contact with the spring, the cam piston configured to abut the distal surface of the compression tab to move the compression tab proximally.

6. The apparatus according to claim 1, wherein the housing is configured to be operably coupled to a source of electrosurgical energy for delivering the electrosurgical energy to tissue via the end effector.

7. The apparatus according to claim 1, wherein the at least one actuator is configured to receive an input for rotating the end effector about a longitudinal axis.

8. An apparatus for remotely activating an end effector of an articulating surgical instrument, the apparatus comprising:
   a housing including at least one actuator configured to receive an input for remotely activating an end effector of an articulating surgical instrument; and
   a driving assembly disposed within the housing, the driving assembly including:
      a spring configured to be compressed in response to the least one actuator receiving the input to cause a drive wire to activate the end effector;
      a compression tab disposed distal to the spring and configured to bias a distal end of the spring; and
      a cam piston configured to cause the compression tab to compress the spring, thereby causing the drive wire to activate the end effector, wherein:
         the cam piston is configured to abut the compression tab and move the compression tab proximally to compress the spring, thereby causing the drive wire to move a cam pin through a cam slot disposed through at least one jaw member of the end effector for activating the end effector; and
         the spring stretches as a result of the end effector being disposed in an articulated position thereby placing the drive wire under increased tension as a result of a spring force on the stretched spring.

9. An apparatus for remotely activating an end effector of an articulating surgical instrument, the apparatus comprising:
   a housing including at least one actuator configured to receive an input for remotely activating an end effector of an articulating surgical instrument; and
   a driving assembly disposed within the housing, the driving assembly including a spring configured to be compressed in response to the least one actuator receiving the input to cause a drive wire to activate the end effector, wherein the spring stretches as a result of the end effector being disposed in an articulated position thereby placing the drive wire under increased tension as a result of a spring force on the stretched spring, wherein the end effector includes a pair of opposable jaw members and the driving assembly is configured to cause the pair of opposable jaw members to maintain a closure pressure in the range of about 3 kg/cm2 to about 16 kg/cm2 on tissue grasped between the pair of opposable jaw members when the end effector is articulated.

* * * * *